United States Patent [19]

Luetzelschwab

[11] 4,361,520

[45] Nov. 30, 1982

[54] REFINEMENT OF SULFONATED HYDROCARBONS

[75] Inventor: Wayne E. Luetzelschwab, Littleton, Colo.

[73] Assignee: Marathon Oil Company, Findlay, Ohio

[21] Appl. No.: 193,069

[22] Filed: Oct. 2, 1980

Related U.S. Application Data

[63] Continuation-in-part of Ser. No. 61,130, Jul. 26, 1979, abandoned.

[51] Int. Cl.³ .......................................... C07C 143/24
[52] U.S. Cl. ............................ 260/505 P; 260/505 R; 260/505 S
[58] Field of Search .............. 260/505 S, 505 P, 505 R

[56] References Cited

U.S. PATENT DOCUMENTS 4,144,266  3/1979  Plummer et al. .................. 260/505

Primary Examiner—Alan Siegel
Attorney, Agent, or Firm—Jack L. Hummel

[57] ABSTRACT

In a process for the production of sulfonated hydrocarbon from a petroleum feedstock, e.g., crude oil or gas oil, enhanced separation of unreacted free hydrocarbon from the sulfonate product is obtained by two separations. The acidic product obtained from the sulfonation of the hydrocarbon is subjected to an incomplete separation from the unreacted hydrocarbon wherein from about 7 to about 12 percent by volume of the free unreacted hydrocarbon is retained in the product. Thereafter, the product is neutralized and subjected to a final separation in which the remainder of free unreacted hydrocarbon is removed from the sulfonated product.

15 Claims, 2 Drawing Figures

REFINEMENT OF SULFONATED HYDROCARBONS

CROSS-RELATED PATENT APPLICATIONS

This application is a continuation-in-part of patent application Ser. No. 061,130 filed July 26, 1979 now abandoned.

TECHNICAL FIELD

This invention relates to the sulfonation of hydrocarbons, e.g., petroleum fractions and crude oils, and, more specifically, to a process for the separation of unreacted hydrocarbon from the final sulfonate product.

BACKGROUND ART

Prior Art Statement

Single extraction of unreacted hydrocarbons from petroleum sulfonates is well-known in the art, for example, U.S. Pat. Nos. 3,493,048 and 3,504,744. Re. 22,548 to Brandt uses water to cause the separation of aqueous sulfuric and sulfonic acids and then uses sodium chloride to extract these acids from organic sulfonic acids. Thereafter, the organic sulfonic acids are neutralized. Brandt also discloses the use of solvents such as ethyl alcohol, dioxane, acetone, etc., in the extraction process.

Gale, et al in U.S. Pat. No. 3,653,437 teaches a single solvent process for the removal of unreacted oils from neutralized petroleum sulfonate surfactant mixtures. Isopropyl alcohol is the preferred solvent of Gale's process. The art also discloses the extraction of unreacted hydrocarbons from petroleum sulfonates either prior to or after the neutralization of the sulfonates, e.g., U.S. Pat. No. 4,144,266. Extraction solvents of water, alcohol, low molecular weight hydrocarbons or mixtures of these are generally preferred.

However, the single extractions of unreacted oil taught by the prior art are incomplete in that over a period of several weeks additional unreacted oil, residual raffinate, of up to about 4 percent will separate from the sulfonate product. The presence of this unreacted oil adversely affects the filterability of a slug containing the sulfonate, e.g., a micellar dispersion, which is used in an oil recovery process.

It is an object of the present invention to effect a complete separation of free unreacted hydrocarbon and residual raffinate from the sulfonate by a two step separation process. Not only does this improve the filterability of a slug containing the sulfonate which is used in an oil recovery process and result in a savings through the recovery of valuable oil, but as a result of the incomplete initial separation of the present process, additional savings are realized through a decrease in settling times and size of settling tanks normally required for a two step separation.

DISCLOSURE OF THE INVENTION

Sulfonated hydrocarbons are refined in a two step separation process to remove unreacted hydrocarbons. First, the acidic hydrocarbon sulfonate is subjected to a partial separation from free unreacted hydrocarbon wherein the acidic hydrocarbon sulfonate phase retains a portion of the free unreacted hydrocarbon, generally from about 7 to about 12 percent by volume. Thereafter, the acidic sulfonate is neutralized and the remaining free unreacted hydrocarbon is separated from the hydrocarbon sulfonate product. If, during the initial separation, a complete separation is obtained between the acidic hydrocarbon product and the free unreacted hydrocarbon, then a portion of the unreacted hydrocarbon must be readded to the acidic sulfonate prior to the neutralization step. The presence of a portion of the free unreacted hydrocarbon in the acid sulfonate product after the first separation is necessary to reduce the separation time needed to separate the neutralized sulfonated product from free unreacted hydrocarbon including any residual raffinate.

The process of the present invention is particularly useful in the production of crude oil and gas oil sulfonates wherein over a period of time residual raffinate continues to separate from the neutralized sulfonate product. While such sulfonates produced by this invention are intended to find their primary use in oil recovery processes, they, or fractions thereof, are also useful in other known applications of sulfonates, such as flotation, cutting oils and insecticide carriers.

BEST MODE FOR CARRYING OUT THE INVENTION

Figure 1:
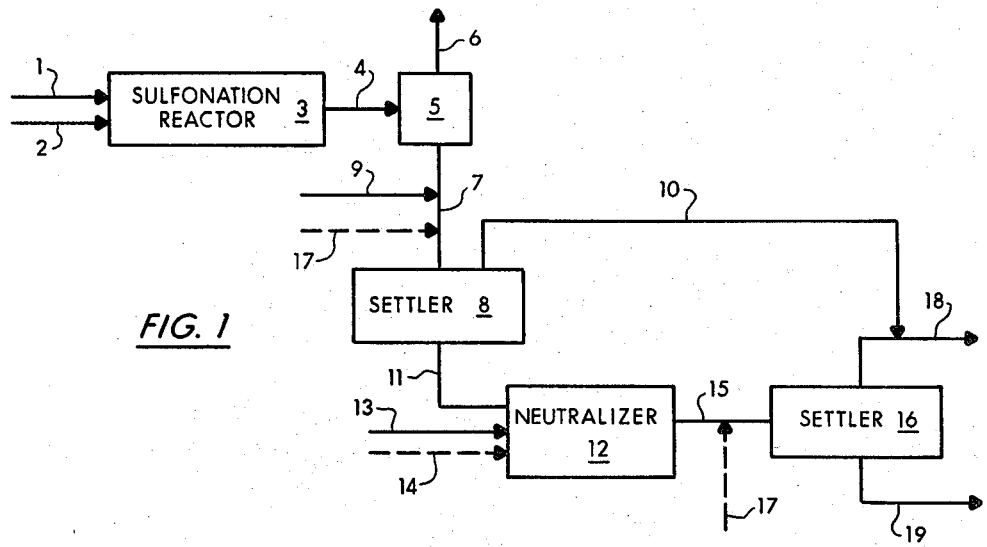
FIG. 1 is a schematic representation of the process of the present invention.

The process of the present invention is applicable to any process for the sulfonation of hydrocarbons wherein not all of the hydrocarbons are sulfonated and wherein unreacted hydrocarbon as a residual raffinate continues to separate from the neutralized sulfonate product, over a period of days to weeks. It is especially beneficial when mixed hydrocarbons, such as crude oils and fractions of crude oil, e.g., gas oils, are sulfonated to produce petroleum sulfonates.

The term "crude oil" as used herein includes whole crudes, crude oils which have been topped to remove the lighter ends having boiling points below about 150° C. and preferably below about 315° C. and mixtures of whole and topped crude oils. The crude oils may be pure hydrocarbons or may contain sulfur, halogen and nitrogen moieties. Preferred crude oils are those with aromatic or olefinic portions having molecular weights in the range of from about 200 to about 1,000, preferably from about 300 to about 800 and more preferably about 350 to about 500. The percent aromatics and olefins in the crude oil is preferably from about 10 to about 95, more preferably from about 20 to about 80 and most preferably from about 25 to about 50 weight percent. The term "gas oil" as used herein refers to that fraction of a crude oil which has a boiling point range of from about 205° C. to about 650° C. and which has an average molecular weight of from about 250 to about 700, an aliphatic to aromatic proton ratio (A/AP) from 5 to about 50 moles per mole and wherein from about 30 to about 100 percent of the hydrocarbons contained in the gas oil fraction contain aromatic portions wherein the A/AP ratio of the aromatic portion is about 3 to about 20 moles per mole. Preferably the average molecular weight of the gas oil will be from about 300 to about 500 and preferably from about 350 to about 450. The A/AP ratio will preferably be from about 10 to about 45 and more preferably from about 15 to about 40. Additionally, the aromatic content of the gas oil is preferably from about 40 to about 80 percent and more preferably from about 40 to about 60 percent and the A/AP ratio of the aromatic portion is preferably from about 4 to about 18 moles per mole.

For the purposes of this invention, the terms "free unreacted hydrocarbon" and "raffinate" are used interchangeably and they refer to the unreacted hydrocarbon contained in either the acid petroleum oil sulfonate or the neutralized petroleum oil sulfonate as a separate phase which readily separates from the ptroleum oil sulfonate. The term "dissolved hydrocarbon" refers to that portion of the unreacted hydrocarbon which is a part of the petroleum oil sulfonate phase, e.g., dissolved or held in the petroleum oil sulfonate phase by miscelles. The term "residual raffinate" refers to a portion of the dissolved hydrocarbon that, although initially a part of the petroleum oil sulfonate phase, is not stable and is slowly released to form a separate phase of unreacted hydrocarbon. This release continues for several weeks resulting in up to about 4 percent of the total volume of the petroleum oil sulfonates separating as a residual raffinate phase.

Upon the sulfonation of the petroleum feedstock or the neutralization of the sulfonated petroleum feedstock, emulsions are formed which upon settling result in the disappearance of the emulsion layer and the formation of two or three readily apparent phases. One phase is the raffinate phase, another phase is the petroleum sulfonate phase and, when a third phase is formed, it is a brine phase. It is the raffinate phase, which is formed upon the disappearance of the emulsion layer, which is the free unreacted hydrocarbon. At this point, the petroleum sulfonate phase will contain dissolved hydrocarbons, a portion of which, if allowed to settle after the formation of the free unreacted hydrocarbon, will continue to separate into a residual raffinate phase for a time period which may be several weeks.

The process of the present invention is directed toward petroleum sulfonates which contain residual raffinate. The present invention provides an efficient process for the elimination of a residual raffinate by first incompletely separating the free unreacted hydrocarbon from an acid petroleum sulfonate, then neutralizing the acid petroleum sulfonate and separating the free unreacted hydrocarbon therefrom. The first incomplete separation significantly speeds up the second separation with the second separation removing any residual raffinate along with the free unreacted hydrocarbon. To the extent that the final petroleum sulfonate product may still contain dissolved hydrocarbons, they are stable within the petroleum sulfonate product and will not separate out over time.

After the sulfonation of the petroleum feedstock, the acid sulfonate product is allowed to settle in order to effect a separation between the acid sulfonate and the free unreacted hydrocarbon. The separation is usually expedited by the use of an extraction solvent in an amount which is sufficient to extract sulfonate from unreacted hydrocarbon. Examples of suitable extraction solvents include water, low molecular weight aliphatic or halogenated alcohols, ketones, ethers, and semipolar hydrocarbons, such as benzene and toluene. Preferably, the amount of salts and unreacted hydrocarbon in the final product are controlled by regulating the extraction solvent to reaction product ratio in the makeup of the extraction solvent. Therefore, generally from about 0.1 to about 3, preferably from about 0.3 to about 1.5 and more preferably from about 0.6 to about 1 kilogram of extraction solvent per kilogram of the acid sulfonate product mixture or the neutralized sulfonate product are used. It is preferred that the extraction solvent be water or an aqueous alcohol. When the extraction solvent is an aqueous alcohol, it is preferred that it be ethanol or isopropyl alcohol. When the aqueous alcohol solution is ethanol it preferably contains from about 20 to about 50 percent by weight ethanol with the total amount of ethanol not exceeding about 55 to about 60 percent by weight. When the aqueous alcohol solution is of isopropyl alcohol, it preferably contains from about 50 to about 80 percent by weight isopropyl alcohol and more preferably from about 55 to about 75 percent by weight isopropyl alcohol. Generally, water is used as the extraction solvent for sulfonated crude oil and an aqueous alcohol solution is utilized for a gas oil sulfonate.

Either two or three phases will result from the addition of the extraction solvent. From top to bottom, these include a raffinate phase consisting primarily of free unreacted hydrocarbon, an extract phase containing most of the petroleum sulfonate product and dissolved hydrocarbon and, depending upon whether alcohol is used, a brine phase containing salts and water. The extraction solvent, if any is present, is separated from the raffinate and extract phases, for example, by stripping. If water is the extraction solvent, it will generally remain with the raffinate phase.

After the addition of the extraction solvent, the water and acid sulfonate product mixture is permitted to settle until the acid sulfonate phase contains a portion of the free unreacted hydrocarbon, generally from about 7 to about 12 percent by volume, which causes a faster separation between the unreacted hydrocarbons and the neutralized sulfonate product than is possible if a complete separation between the free unreacted hydrocarbon and the sulfonic acids or extract phase is obtained. If sufficient raffinate is not retained, then a portion of the raffinate should be readded to the acid sulfonate mixture. The presence of greater or lesser amounts of raffinate will not prevent the complete separation of raffinate from the sulfonated product; however, more time will be required for the second separation. The amount of free unreacted hydrocarbon left with the sulfonic aid phase is dependent upon a variety of factors including the particular petroleum feedstock sulfonated, temperature of the separation, the composition of the acid sulfonate phase, for example, its water and sulfonate composition and degree of disulfonation, etc. Thus, the amount of free unreacted hydrocarbon left with the sulfonic acid phase, which will give a faster separation between the neutralized sulfonate and free unreacted hydrocarbon, is dependent upon these various fators and can be readily determined for each sulfonated feedstock by one skilled in the art. However, generally from about 7 to about 12 volume percent of free unreacted left with the sulfonic acids is sufficient to effect the process of this invention.

The thus partially refined sulfonic acid mixture is then neutralized with sufficient base, preferably a monovalent base, such as sodium or potassium hydroxide or ammonia, to form a neutralized petroleum sulfonate. Additional extraction solvent can be added during the neutralization process, as for example, when it is used as the carrier of the neutralizing agent.

After neutralization to obtain petroleum sulfonate, the petroleum sulfonate mixture is allowed to settle to effect the separation between the remaining free unreacted hydrocarbon and the petroleum sulfonate. The free unreacted hydrocarbon as a raffinate is then removed from the sulfonate product. No further separation of unreacted hydrocarbon as a residual raffinate from the petroleum sulfonate will thereafter occur.

The amount of time required for each of the separations of the present refinement process is dependent upon several parameters, for example, size of the settling tank, amount of product being subjected to the process, temperature, and amount of free unreacted hydrocarbon. The amount of free unreacted hydrocarbon is affected, for example, by the composition of the feedstock sulfonated and the amount of sulfur trioxide used in the sulfonation process. Since the interaction of these parameters are understood by those skilled in the art, the amount of time for each separation in a given process is readily determined by one skilled in the art. Generally, the first partial separation of the acidic product will take from about 1 to about 2 hours per foot of emulsion. The time required for the second separation will be affected by the amount of raffinate the neutralized product contains. When from about 7 to about 12 percent by volume raffinate is present, the second separation will generally take from about 0.3 to about 0.6 hours per foot of emulsion.

The separation of the unreacted hydrocarbon from the sulfonate can be done as a batch operation or as a continuous operation.

Sulfonation reactors which are conventionally utilized in processes for the sulfonation of hydrocarbons including, for example, falling film, scraped surface and stirred tank reactors, may be used in the process of this invention. In those instances where a sulfur trioxide diluent is used, a back mixed tubular reactor is preferred and the materials introduced into the tubular reactor should be in turbulent flow.

It is preferred that an anhydrous sulfur trioxide feed that is free of impurities such as sulfuric acid, which can cause deleterious side reations, be used. From about 5 to about 30, preferably from about 7 to about 20 and more preferably from about 8 to about 15 kilograms of sulfur trioxide is fed into the sulfonation reactor per 100 kilograms of crude oil or gas oil. The sulfur trioxide can be either a liquid or vaporized state however, the vaporized state is preferred.

The sulfur trioxide can be diluted with liquid or gaseous low molecular aliphatics, sulfur dioxide, air, nitrogen or other inert gases. The ratio of the diluent to sulfur trioxide should be from about 0 to about 10, more preferably from about 1 to about 6 and most preferably from about 2 to about 4 moles of diluent per mole of sulfur trioxide. The preferred diluent for the sulfur trioxide is a recycle of the light ends containing a mixture of sulfur dioxide and light hydrocarbons which are obtained from the sulfonation reactor by a one stage flash.

A reaction solvent, such as ethylene dichloride, trichloroethylene, nitrobenzene, nitropropane, naphtha, hexane and similar substantially inert polar solvents can be introduced into the reactor to dissolve the sulfonic acids in the unreacted hydrocarbons. in addition to acting as a solvent for the sulfonic acids, the solvent can also act as a diluent for the sulfur trioxide. The desirability of a specific solvent is dependent upon the reactivity of the petroleum feedstock being sulfonated. Heavy viscous petroleum feedstocks, such as gas oils, often require a solvent while less viscous crude oils can be sulfonated with or without a solvent. A preferred diluent for less viscous crudes, e.g., whole crude oil, is recycled sulfonic acids from the sulfonation reactor which contain sulfur dioxide and light hydrocarbons. Preferred solvents, which may also act as diluents, for more viscous petroleum feedstocks, e.g., heavy vacuum gas oils, are ethylene dichloride, naphtha and hexane.

Generally, the solvent is used in a concentration of from about 0 to about 20 kilograms, preferably from about 1 to about 10 kilograms and more preferably from about 3 to about 8 kilograms per kilogram of sulfur trioxide. Except when the solvent or the diluent is a sulfonic acid, it is preferred that the reaction solvent or diluent be removed, e.g., by steam stripping, prior to the separation of any unreacted hydrocarbons from the sulfonated hydrocarbon.

The reactor conditions are not narrowly critical. The temperature will normally be in the range of from about 27° C. to about 120° C., preferably from about 38° C. to about 93° C. and more preferably from about 55° C. to about 82° C. Pressures will range from about 0.01 to about 150, preferably from about 0.15 to about 75 and more preferably from about 0.2 to about 5 atmospheres. The reaction times will be from about 0.001 to about 3600, preferably from about 0.01 to about 360 and more preferably from about 0.02 to about 60 seconds.

Additional materials can be introduced into the sulfonation reactor. These include known catalysts which do not appear to be needed but may be used if desired, and sulfonation additives which, inter alia, may aid in controlling the equivalent weight distribution of the product mixture. The additives are useful in amounts ranging from about 0 to about 20, preferably from about 1 to about 15 and more preferably from about 2 to about 20 kilograms of additive per 100 kilograms of petroleum feedstock. The additives are often sulfonated or sulfated and become a component of the product mixture. The additives are incorporated in the feedstocks before or during sulfonation.

Useful additives include aromatic hydrocarbons, olefinic hydrocarbons or oxygenated hydrocarbons which preferably have molecular weights in the range of from 200 to about 1,000, more preferably from about 300 to about 800 and most preferably 350 to about 500. Specific examples of additives include oxo alcohol bottoms which are described by Hatch, L.F., *Higher Oxo Alcohols,* Enjay Co., Inc. 1957 and *Industrial and Engineering Chemistry,* Vol. 51, No. 3, pp. 257-258 ; oxo alcohols alkylated with from about 1 to about 50 moles of alkylene oxides, such as ethylene or propylene oxide catalytic cycle oil aromatics, see U.S. Pat. No. 3,317,442; and ultraformer polymer bottoms which are mixtures of alkylated benzenes and asphaltenes.

If the hydrocarbon feedstock contains wax, then an extractant, such as kerosene or naphtha, may be added to the partially separated acidic sulfonate prior to the neutralization of the acidic sulfonate. Kerosene is added in an amount of from about 0.05 to about 0.5 kilograms per kilogram of acid sulfonate product.

The refined petroleum sulfonates produced by the process of this invention are useful in the formulation of micellar dispersions comprised of hydrocarbon, water and petroleum sulfonate, which are utilized in oil recovery processes. Examples of such micellar dispersions include micellar flooding of subterranean reservoirs with systems of the type taught by H. J. Hill, J. Reisberg, and G. L. Stegemeier, *J. Pet. Tech.,* 186 (Feb., 1973), within relatively dilute aqueous "solutions" of surfactant and/or cosurfactant are injected; the process of R. L. Reed, et al. U.S. Pat. No. 3,885,628 wherein a multiphase system is injected; U.S. Pat. No. 3,082,822 issued to L. W. Holm, et al. wherein substantially small slugs of anhydrous soluble oils are alternately injected with small slugs of water or other aqueous media; U.S. Pat. No. 3,682,247 to Jones; 3,687,201 to Son, et al. 3,740,343 to Jones, et al; 3,956,372 to Coleman, et al; 3,964,548 to Schroeder, et al; 3,997,451 to Plummer, et al; and 4,013,125 to Plummer, et al. Petroleum sulfonates are also useful in other types of suractant floods used in oil recovery processes.

FIG. 1 exemplifies the process of the present invention. The petroleum hydrocarbon feedstock and sulfur trioxide vapor enter a sulfonation reactor 3 through lines 1 and 2, respectively. The resultant product mixture containing sulfonic acids and unreacted oils is conducted by conduit 4 to a liquid/gas separator 5. Sulfur dioxide, light hydrocarbons and diluent solvent, when it is used, are separated and removed from the sulfonated product mixture via conduit 6. If desired, these gaseous products, e.g., sulfur dioxide and light hydrocarbons, can be recycled to the sulfonation reactor for use as a reaction solvent. If a diluent solvent is used which remains in the liquid phase, it can be removed by any appropriate means at any time later in the process. While the sulfonated product mixture is being conducted through conduit 7 to settler 8, an extraction solvent 9 is added to the mixture. The extraction solvent and sulfonated product mixture are then allowed to separate in settler 8 until the acidic sulfonate product mixture contains from about 7 to about 12 percent by volume of free unreacted hydrocarbon. The free unreacted hydrocarbon is then removed by conduit 10 and ultimately recombined with the raffinate obtained by the separation of the neutralized petroleum sulfonate. The sulfonic acid from settler 8 are conducted by conduit 11 to neutralizer 12, wherein the sulfonic acids are neutralized by the addition of a base supplied through conduit 13. Water can be added, if desired, to the neutralizer, through a separation conduit 14 or via conduit 13 as a carrier for the base. The sulfonation product is then conducted through line 15 to another settler 16. If needed, kerosene or other wax extractant, can be added to the sulfonated product via conduit 17 prior to its introduction in either settler 8 or settler 16. The addition of this kerosene is as an adjunct to extract waxes from the petroleum sulfonate. The petroleum sulfonate is then allowed to settle until a complete phase separation has occurred between the remaining free unreacted hydrocarbon including any residual raffinate and the petroleum sulfonate. Thereafter, the remaining free unreacted hydrocarbon is separated from the neutralized sulfonate product and removed from the settler via conduit 18. The neutralized petroleum sulfonate is removed via conduit 19 and thereafter incorporated into a micellar dispersion for use in an oil recovery process.

EXAMPLES

The following examples are illustrative of the invention and are comparative in nature. Example 1 demonstrates the presence of residual raffinate in a crude oil sulfonate which was not prepared in accordance with the process of the present invention. Examples 2 and 4 demonstrate the effect of an incomplete separation between the raffinate phase containing free unreacted hydrocarbon and the acid sulfonate has on the speed of separation of the neutralized sulfonate product from unreacted hydrocarbon. Example 3 demonstrates that two separations are needed to prevent the occurrence of or remove residual raffinate from a petroleum sulfonate which forms or contains residual raffinate.

EXAMPLE 1

Samples of different crude oils were prepared by sulfonating each crude oil at a rate of about 450 kilograms per hour with 45 kilograms per hour of sulfur trioxide at a temperature of about 80° C. The vapor stream was then separated from the liquid stream containing sulfonic acids, sulfuric acid, sulfurous acid and unreacted oils. Then, the liquid stream was mixed with about 400 kilograms of fresh water per hour and enough ammonia to obtain a pH of about 6. In some cases, approximately 220 kilograms of kerosene per hour were also added at this point to reduce the final wax content of the crude oil sulfonate product. This neutralized liquid stream was allowed to settle for about 4 hours in a settling tank having a 3800 liter capacity in order to effect a phase separation between the raffinate (unreacted free hydrocarbon) and the crude oil sulfonate (COS). These two phases were separated and the crude oil sulfonate contained no detectable free unreacted hydrocarbon as it left the settler. Thereafter, the COS was allowed to settle for the time indicated in Table 1. The amount of residual raffinate which separated from the COS during this time period is also given in Table 1. The residual raffinate continued to come out of solution for several days and often for several weeks.

TABLE 1

| Sample | Crude Oil Feedstock | Time Period (Hours) | Residual Raffinate (Vol. %) |
|---|---|---|---|
| 1 | Bailey/North Crawford County, Indiana (Kerosene added during neutralization) | 0 | 0 |
|  |  | 3 | 0.5 |
|  |  | 5 | 1.0 |
|  |  | 7 | 1.3 |
|  |  | 8 | 1.4 |
|  |  | 27 | 1.9 |
|  |  | 51 | 2.2 |
|  |  | 121 | 2.6 |
|  |  | 244 | 2.6 |
|  |  | 364 | 2.7 |
| 2 | Bailey/North Crawford County, Indiana (Kerosene added during neutralization) | 0 | 0 |
|  |  | 3 | 0.5 |
|  |  | 5 | 1.1 |
|  |  | 7 | 1.4 |
|  |  | 8 | 1.4 |
|  |  | 27 | 1.8 |
|  |  | 97 | 2.4 |
|  |  | 220 | 2.6 |
|  |  | 340 | 2.6 |
| 3 | Muddy Creek | 42 | 2.0 |
| 4 | Indiana | 50 | 0.8 |
| 5 | Bailey | 111 | 2.8 |
| 6 | North Crawford County | 77 | 2.3 |
| 7 | Bailey/Muddy Creek | 216 | 2.8 |
| 8 | Bridgeport | 168 | 1.0 |

EXAMPLE 2

Figure 2:
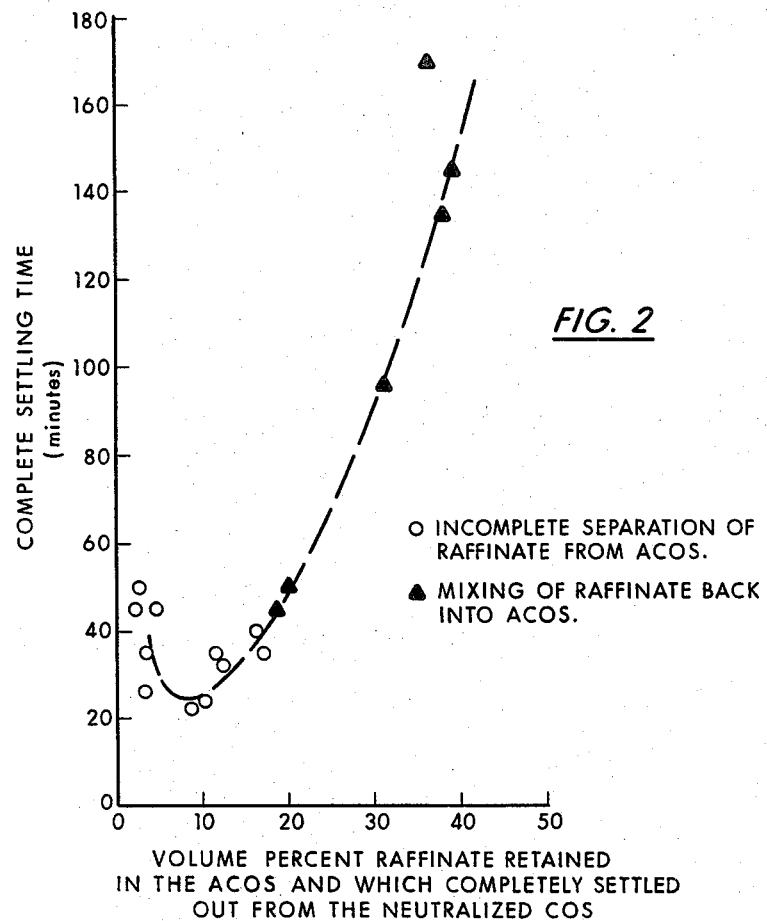
FIG. 2 is a graphic representation of the settling time of the neutralized sulfonate as a function of retained raffinate.

A crude oil sulfonate was prepared by sulfonating 450 kilogram per hour of Crawford County, Illinois crude oil with 45 kilograms of sulfur trioxide at a temperature of 80° C. Samples of the thus obtained acidic crude oil sulfonate (ACOS) were allowed to settle and separate into raffinate and acidic crude oil sulfonate phases. The two phases were then subjected to an incomplete separation and the amount of raffinate which the separated acidic crude oil sulfonate contained is given in FIG. 2. With some of the samples, additional raffinate was remixed into the already separated acidic crude oil sulfonate. Thereafter, all of the samples were neutralized with sufficient ammonia to obtain a crude oil sulfonate/raffinate mixture having a pH about 6–6.5. Each of the samples was allowed to settle and the time required for complete separation between the neutralized crude oil sulfonate and the raffinate is given in FIG. 2.

EXAMPLE 3

Four hundred fifty kilograms per hour of a Crawford County, Illinois crude oil was reacted with 45 kilograms per hour of sulfur trioxide at a temperature of 82° C. After separating off the vapor stream, composed mostly of light hydrocarbons and sulfur dioxide, the remaining stream, i.e., as acid crude oil sulfonate mixture, composed mostly of sulfonic acids, sulfuric acid, sulfurous acid and unreacted hydrocarbons, was processed in the following ways:

Sample 1

The acid crude oil sulfonate mixture was mixed with 450 kilograms per hour of fresh water and enough ammonia to give a pH of about 6, then allowed to separate over four hours at 70° C. in a 3800 liter settler. Four samples of the crude oil sulfonate stream from the settler were held for varying time periods at 70° C. in volumetric flasks to determine how much residual raffinate would separate into a top phase. A residual raffinate layer of 1.1 percent by volume was obtained from a sample held for twenty hours; 1.6 and 1.7 percent by volume residual raffinates were obtained from two samples held for three days and a sample held for 28 days showed a raffinate layer of 2.0 percent by volume.

The average time required for complete settling of the neutralized stream into a raffinate phase and the petroleum sulfonate phase was 95 minutes. The settling time was obtained by taking about foot high samples of the neutralized stream in 1000 milliliter graduated cylinders, maintaining the temperature of the samples at 70° C. and then measuring the time required to obtain the phase separation.

Sample 2

The acid crude oil sulfonate mixture was treated with 450 kilograms per hour of fresh water, then this mixture was settled at 60° C. in a 3400 liter settler with a residence time of about 3.5 hours and separated into a raffinate stream and an acid crude oil sulfonate stream containing no free unreacted hydrocarbon. The two streams from the settler, the raffinate and acid crude oil sulfonate, were then recombined and neutralized with ammonia to a pH of about 6. This mix, which contained about 38 percent by volume raffinate, was then put through a second settler of 3800 liter capacity at 70° C. and a residence time of about 4 hours. After separation of the neutralized COS and raffinate, samples of the crude oil sulfonate were held at 70° C. in volumetric flasks for several hours, at which time about 0.3 volume percent residual raffinate separated to the top of the crude oil sulfonate. More raffinate would have separated out had this sample been held longer at 70° C.

Sample 3

Fresh water, at a rate of 450 kilograms per hour, was added to the acid crude oil sulfonate mixture, then this mixture was allowed to separate in a 3400 liter settler with a residence time of about 3.5 hours at a temperature of 50° C. A stream of clear raffinate was removed from the top of the settler. The acid crude oil sulfonate stream from the bottom of the settler was not clear and it contained about 40 percent of the total raffinate. This stream was neutralized with ammonia to a pH of about 6, and then put through a second settler of 3800 liter capacity at 70° C. and a residence time of about 5 hours. Samples of this neutralized stream entering the second settler were batch settled at 70° C. and showed 10.3 and 16.4 volume percent raffinate. Samples of the raffinate free crude oil sulfonate stream were held at 70° C. in volumetric flasks for several hours. No residual raffinate was observed. Observation for several more hours still showed no residual raffinate.

Sample 4

The run conditions were the same as those of Sample 3, except that the first settler was at about 60° C. and the acid crude oil sulfonate from the first settler contained about 10 percent of the total raffinate. Samples of the neutralized stream entering the second settler were batch settled at 70° C. and showed 3.5, 8.8 and 3.3 volume percent raffinate. Samples of the raffinate free crude oil sulfonate from the second settler were held at temperature in volumetric flasks for several hours. No residual raffinate separated to the top. Observation for several more hours still showed no residual raffinate.

EXAMPLE 4

Four hundred fifty kilograms per hour of a Crawford County, Illinois crude oil was reacted with 45 kilograms per hour of sulfur trioxide at 80° C. After separating off the vapor stream, composed primarily of light hydrocarbons and sulfur dioxide, the remaining stream, i.e., an acid crude oil sulfonate mixture, composed mostly of sulfonic acids, sulfuric acid, sulfurous acid and unreacted hydrocarbons was mixed with 450 kilograms per hour of fresh water and put into a 3400 liter settler for a residence time of about 3.5 hours and separated into a raffinate and extract phase. This acid separation and a second separation at nearly neutral conditions were varied, as described in each of the following samples.

Sample 1

In this sample, two separate complete acid separations were conducted at a temperature of 50° C. (Sample 1A) and 70° C. (Sample 1B). Both resulted in a clear raffinate stream and a nearly clear acid crude oil sulfonate stream. Both acid crude oil sulfonate streams were neutralized with ammonia to a pH of about 6 and then allowed to reside for about 6 hours in a second settler at a temperature of 70° C. A sample of about one-foot height of each of the neutralized crude oil sulfonate was taken in a 1000 milliliter graduated cylinder and held at 70° C. Sample 1A took 45 minutes to completely separate and 2.4 percent by volume of raffinate was removed; Sample 1B took 50 minutes to completely separate and 2.9 percent by volume of raffinate was removed.

Samples 2–4

Additional samples were subjected to the same two step separation process of Sample 1 with the exception that the acid separation was not complete. The amount of raffinate left in the acid crude oil sulfonate is indicated in Table 2 as are the results of the neutralized separation.

TABLE 2

| Temperature of Acid Separation | Raffinate left in ACOS (vol. %) | Settling time of Neutralized COS (minutes) | Raffinate Removed in 2nd Separation (vol. %) |
|---|---|---|---|
| 50° C. | 7–8 | 24 | 10.3 |
| 70° C. | 5.5–6.5 | 22 | 8.8 |
| 70° C. | 14 | 40 | 16.4 |

Sample 5

In this sample a complete acid separation was conducted at a temperature of 60° C. The separated raffinate was recombined with all of the acid crude oil sulfonate stream and then neutralized with ammonia to a pH of about 6. This neutralized stream was flowed into a second settler where it settled for 4 hours at a temperature of 70° C. A sample of one-foot height taken of this neutralized inlet stream to the second settler took 135 minutes to completely separate and 38.1 percent by volume of raffinate was removed.

What is claimed is:

1. A process of enhancing the separation of unreacted hydrocarbons from the sulfonated product mixture obtained by contacting about 5 to about 30 grams sulfur trioxide per 100 kilograms of a hydrocarbon selected from the group consisting of crude oils, top crude oils, gas oils and mixtures thereof in a reaction zone at a temperature of from about 27° C. to about 121° C. and a pressure from about 0.01 to about 150 atmospheres for a reaction time of from about 0.001 to about 3600 seconds to form a sulfonated product mixture from which a raffinate comprising free unreacted hydrocarbons separates, said method comprising the steps of:
  (a) removing a portion of said raffinate thereby leaving the remainder of said raffinate with said sulfonated product mixture;
  (b) neutralizing with a base said sulfonated product mixture containing said remainder of said raffinate to form a neutralized sulfonated product mixture and a second raffinate; and
  (c) thereafter removing said second raffinate from the neutralized sulfonated product mixture, the remainder of said raffinate in step (a) being in an amount sufficient to enhance the separation rate of said second raffinate and said neutralized sulfonated product mixture thereby enabling the removing of step (c) to take place at a rate faster than that which would take place if substantially all of said raffinate had been removed prior to step (b).

2. The process of claim 1 wherein step (a) comprises removing substantially all of said raffinate and thereafter adding a portion of the raffinate as said remainder to said sulfonated product mixture prior to the neutralizing of step (b).

3. The process of claim 1 or claim 2 further comprising adding an extraction solvent to the sulfonated product mixture prior to step (a).

4. The process of claim 1 or claim 3 wherein the sulfonate product mixture prior to its neutralization contains an amount of said remainder of said raffinate which will cause a separation between the neutralized sulfonate product and free unreacted hydrocarbon to occur at a rate of from about 0.3 to about 0.6 hours per foot of emulsion.

5. The process of claim 1 or claim 3 wherein the sulfonate product mixture prior to its neutralization contains from about 7 to about 12 percent by volume of said remainder of said raffinate.

6. The process of claim 3 wherein the extraction solvent is used in an amount of from about 0.1 to about 3 killograms per kilogram of sulfonated product mixture.

7. The process of claim 6 wherein the extraction solvent is selected from the group consisting of water and a low molecular weight aqueous alcohol.

8. The process of claim 7 wherein the hydrocarbon to be sulfonated is selected from the group consisting of crude oils and topped crude oils and the extraction solvent is water.

9. The process of claim 7 wherein the hydrocarbon to be sulfonated is a gas oil and the extraction solvent is a low molecular weight aqueous alcohol.

10. In a process for the preparation of petroleum sulfonates useful in the preparation of micellar dispersions for supplemental recovery of oil, said sulfonates having an average equivalent weight of from about 350 to about 525, by contacting sulfur trioxide with hydrocarbon selected from the group consisting of crude oils, topped crude oils, gas oils and mixtures thereof at a temperature of from about 38° C. to about 93° C. and a pressure of from about 0.15 to about 75 atmospheres for a reaction time of from about 0.1 to about 360 seconds wherein from about 7 to about 20 kilograms of sulfur trioxide are contacted with each 100 kilograms of hydrocarbon, the improvement comprising:
  (a) partially extracting free unreacted hydrocarbon from the sulfonated product mixture with from about 0.1 to about 3.0 kilograms of an extraction solvent per kilogram of sulfonated product mixture to obtain sulfonated product mixture containing from about 7 to about 12 percent by volume of the free unreacted hydrocarbon;
  (b) neutralizing with a monovalent base the sulfonated product mixture containing from about 7 to about 12 percent free unreacted hydrocarbon;
  (c) permitting the sulfonate product mixture and free unreacted hydrocarbon to separate; and
  (d) removing all of the free unreacted hydrocarbon from the neutralized sulfonated product.

11. The process of claim 10 wherein the extraction solvent is used in an amount of from about 0.3 to about 1.5 kilograms per kilogram of the sulfonated product mixture.

12. The process of claim 10 or claim 11 wherein the extraction solvent is selected from the group consisting of water or a low molecular weight aqueous alcohol solution.

13. The process of claim 12 wherein the hydrocarbon sulfonated is selected from the group consisting of crude oils and topped crude oils and the extraction solvent is water.

14. The process of claim 12 wherein the hydrocarbon feedstock sulfonate is a gas oil and the extraction solvent is a low molecular weight aqueous alcohol selected from the group consisting of aqueous ethanol and aqueous propanol.

15. In a process for the preparation of petroleum sulfonates comprising contacting sulfur trioxide with a hydrocarbon selected from the group consisting of crude oils, topped crude oils, gas oils and mixtures thereof in a reaction zone at a temperature of from about 27° C. to about 121° C. and a pressure of from about 0.1 to about 150 atmospheres for a reaction time of from about 0.001 to about 3600 seconds wherein from about 5 to about 30 kilograms of sulfur trioxide are contacted with each 100 kilograms of hydrocarbon, the improvement comprising:

(a) allowing the sulfonate product mixture to separate into a free unreacted hydrocarbon phase and an acid sulfonated product phase;

(b) separating the sulfonate product mixture into a phase containing a portion of the free unreacted hydrocarbon and an acid sulfonated product phase containing the remainder of the free unreacted hydrocarbon such that the remainder of free unreacted hydrocarbon causes a faster separation between unreacted hydrocarbon and neutralized sulfonate product than is possible if a complete separation were effected between the free unreacted hydrocarbon and the sulfonated product mixture to be neutralized;

(c) neutralizing with a base the acid sulfonated product mixture containing the remainder of the free unreacted hydrocarbon of step (b); and (d) thereafter removing all of the free unreacted hydrocarbon from the neutralized sulfonated product mixture at a rate of from about 0.3 to about 0.6 hours per foot of emulsion.

* * * * *

UNITED STATES PATENT AND TRADEMARK OFFICE
CERTIFICATE OF CORRECTION

PATENT NO. : 4,361,520
DATED : November 30, 1982
INVENTOR(S) : Wayne E. Luetzelschwab It is certified that error appears in the above-identified patent and that said Letters Patent are hereby corrected as shown below:

| | |
|---|---|
| Col. 3, line 10: | Delete "ptroleum" and insert --petroleum--. |
| Col. 3, lines 14 and 15: | Delete "miscelles" and insert --micelles--. |
| Col. 4, line 45: | Delete "aid" and insert --acid--. |
| Col. 5, line 61: | Delete "in" and insert --In--. |
| Col. 6, line 49: | Following "propylene oxide" insert --;--. |
| Col. 6, line 67: | Delete "within" and insert --wherein--. |
| Col. 7, lines 1, 3, and 6: | Following "al." insert --;--. |
| Col. 7, line 36: | Delete "acid" and insert --acids--. |
| Col. 12, line 5: | Delete "killograms" and insert --kilograms--. |

Signed and Sealed this

Twenty-sixth Day of April 1983

|SEAL|

Attest:

GERALD J. MOSSINGHOFF

Attesting Officer

Commissioner of Patents and Trademarks